United States Patent
Akolkar et al.

(10) Patent No.: US 12,241,862 B2
(45) Date of Patent: Mar. 4, 2025

(54) ELECTROCHEMICAL SENSOR FOR LEAD DETECTION

(71) Applicant: CASE WESTERN RESERVE UNIVERSITY, Cleveland, OH (US)

(72) Inventors: Rohan Akolkar, Beachwood, OH (US); Xinyu Liu, Cleveland, OH (US); Kailash Venkatraman, Beachwood, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 770 days.

(21) Appl. No.: 17/480,845

(22) Filed: Sep. 21, 2021

(65) Prior Publication Data

US 2022/0011263 A1    Jan. 13, 2022

Related U.S. Application Data

(63) Continuation-in-part of application No. 16/255,486, filed on Jan. 23, 2019, now Pat. No. 11,125,717.

(60) Provisional application No. 62/620,786, filed on Jan. 23, 2018.

(51) Int. Cl.
  *G01N 27/42* (2006.01)
  *G01N 33/18* (2006.01)
(52) U.S. Cl.
  CPC ......... *G01N 27/42* (2013.01); *G01N 33/1813* (2013.01)
(58) Field of Classification Search
  None
  See application file for complete search history.

(56) References Cited

U.S. PATENT DOCUMENTS 11,125,717 B2 *   9/2021   Akolkar .............. G01N 27/4166
2019/0227030 A1 * 7/2019   Liu ..................... G01N 27/4166

* cited by examiner

*Primary Examiner* — J. Christopher Ball
(74) *Attorney, Agent, or Firm* — Tarolli, Sundheim, Covell & Tummino LLP

(57) ABSTRACT

A sensor for detecting lead in an aqueous solution includes a copper working electrode, a counter electrode, a power supply for applying underpotential deposition of lead onto the copper electrode, a measuring device for providing measurement of a hydrogen evolution reaction (HER) current on the $Pb_{upd}$-modified electrode, and a controller configured to correlate the degree of suppression of the HER current to $Pb_{upd}$ coverage to determine the lead coverage and lead concentration of the solution.

5 Claims, 8 Drawing Sheets

ELECTROCHEMICAL SENSOR FOR LEAD DETECTION

RELATED APPLICATION

This application is a Continuation-in-Part of U.S. Ser. No. 16/255,486, filed Jan. 23, 2019 (Now U.S. Pat. No. 11,125,717), which claims priority from U.S. Provisional Application No. 62/620,786, filed Jan. 23, 2018, the subject matter of which are incorporated herein by reference in their entirety.

BACKGROUND

Lead contamination in drinking water is a worldwide problem affecting people in developing as well as developed countries. While lead contamination levels are routinely monitored at water treatment facilities, many water sources get contaminated with lead during distribution (lead pipes). The Environmental Protection Agency (EPA) has issued a regulation that limits the amount of lead concentration in drinking water to below 15 ppb. To ensure that drinking water is not lead contaminated, different methods are applied for detecting lead concentration in water. The most common methods include colorimetry, atomic absorption spectroscopy (AAS) and inductively coupled plasma (ICP) emission spectroscopy. These techniques can measure the lead concentration accurately; however, these methods are expensive and require access to advanced instrumentation which is accessible only through certified laboratories. Therefore, it is essential to develop a low-cost, portable and reliable lead sensor for use in homes and offices.

SUMMARY

Embodiments described herein relate to a sensor and method for detecting, identifying, quantifying, and/or determining the amount or level of lead in an aqueous solution, and particularly relates to a sensor for detecting, identifying, quantifying, and/or determining the amount or level of lead in an aqueous solution, such as water or other fluids. Advantageously, the sensor enables detection of ppb-levels of $Pb^{2+}$ in water.

The sensor includes a copper working electrode, a counter electrode, a power supply, and a current measuring device. The copper working electrode and counter electrode are configured for placement in the aqueous solution. The power supply is configured to apply underpotential deposition of lead onto the copper electrode. The measuring device provides measurement of a hydrogen evolution reaction (HER) current on the $Pb_{upd}$-modified electrode. The sensor can also include a controller configured to correlate the degree of suppression of the HER current to $Pb_{upd}$ coverage to determine the lead coverage and lead concentration of the solution and provide an output of determined lead concentration in the sample based on the degree of suppression of the HER current to $Pb_{upd}$ coverage and lead coverage to a display device (not shown).

The sensor works on the principle of underpotential deposition of lead onto the copper electrode followed by measurement of the hydrogen evolution reaction (HER) current on the $Pb_{upd}$-modified electrode surface. The degree of suppression of the HER current is correlated to $Pb_{upd}$ coverage, which in turn depends on the $Pb^{2+}$ concentration in solution. The HER current of the lead covered electrode can be compared to the HER baseline current on lead-free electrode to determine the lead coverage and thus the lead concentration of the solution.

In some embodiments, the sensor can include a substrate, a copper working electrode formed on a surface of the substrate, and a counter electrode formed on the surface of the substrate. The counter electrode can include a metalized film, such as gold, platinum, palladium, silver, carbon, alloys thereof, and composites thereof. The films used to form the working electrode and counter electrode can be provided on the surface of the substrate by film printing or sputtering or coating the films on the surface and then optionally laser ablating the films to form the working electrode and counter electrode.

In some embodiment, the copper working electrode can have an irregular needle-like dendrite surface profile that is defined by underlying dendrites of electrodeposited zinc. A sensor as described herein with a copper working with the dendrite surface profile can have decreased lead sensing time compared to sensor with a copper electrode having a planar surface.

DETAILED DESCRIPTION

Unless specifically addressed herein, all terms used have the same meaning as would be understood by those of skilled in the art of the subject matter of the application. The following definitions will provide clarity with respect to the terms used in the specification and claims.

As used herein, the term "quantitative data" or "quantitative level" or "quantitative amount" refers to data, levels, or amounts associated with any dataset components (e.g., markers, clinical indicia,) that can be assigned a numerical value.

As used herein, the terms "control" or "control sample" refer to one or more samples in which the concentration of the lead is known.

Embodiments described herein relate to an electrochemical sensor and method for detecting, identifying, quantifying, and/or determining the amount or level of lead in a sample, and particularly relates to a sensor for detecting, identifying, quantifying, and/or determining the amount or level of lead in a sample, such as tap or drinking water or other aqueous fluids.

Figure 1:
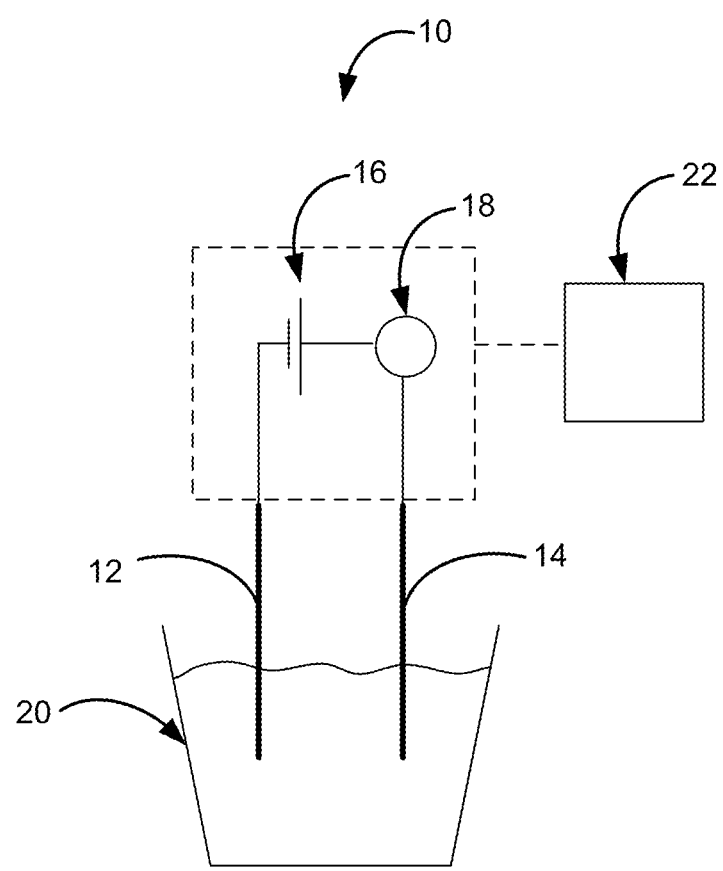
FIG. 1 is a schematic of an electrochemical sensor in accordance with an embodiment described herein.

FIG. 1 is a schematic illustration of an embodiment of the sensor 10 described herein. The sensor 10 includes a copper working electrode 12, a counter electrode 14, a power supply 16, and a current measuring device 18. The copper working electrode 10 and counter electrode 12 are configured for placement in an aqueous solution 20. The power supply 16 is configured to apply underpotential deposition of lead onto the copper working electrode 12. The measuring device 18 (e.g., ammeter) provides measurement of a hydrogen evolution reaction (HER) current on the $Pb_{upd}$-modified working electrode 12. The sensor 10 can also include a controller 22 configured to correlate the degree of suppression of the HER current to $Pb_{upd}$ coverage to determine the lead coverage and lead concentration of the solution and provide an output of determined lead concentration in the sample based on the degree of suppression of the HER current to $Pb_{upd}$ coverage and lead coverage to display device (not shown).

In some embodiments, the electrochemical sensor 10 can include a reference electrode (not shown) and a measuring device (not shown) for applying voltage potentials to the working electrode and counter electrode and measuring the hydrogen evolution current of the lead covered working electrode and the hydrogen evolution baseline current on lead-free electrode to determine the level of the lead in a sample, such as a drinking water.

Figure 2:
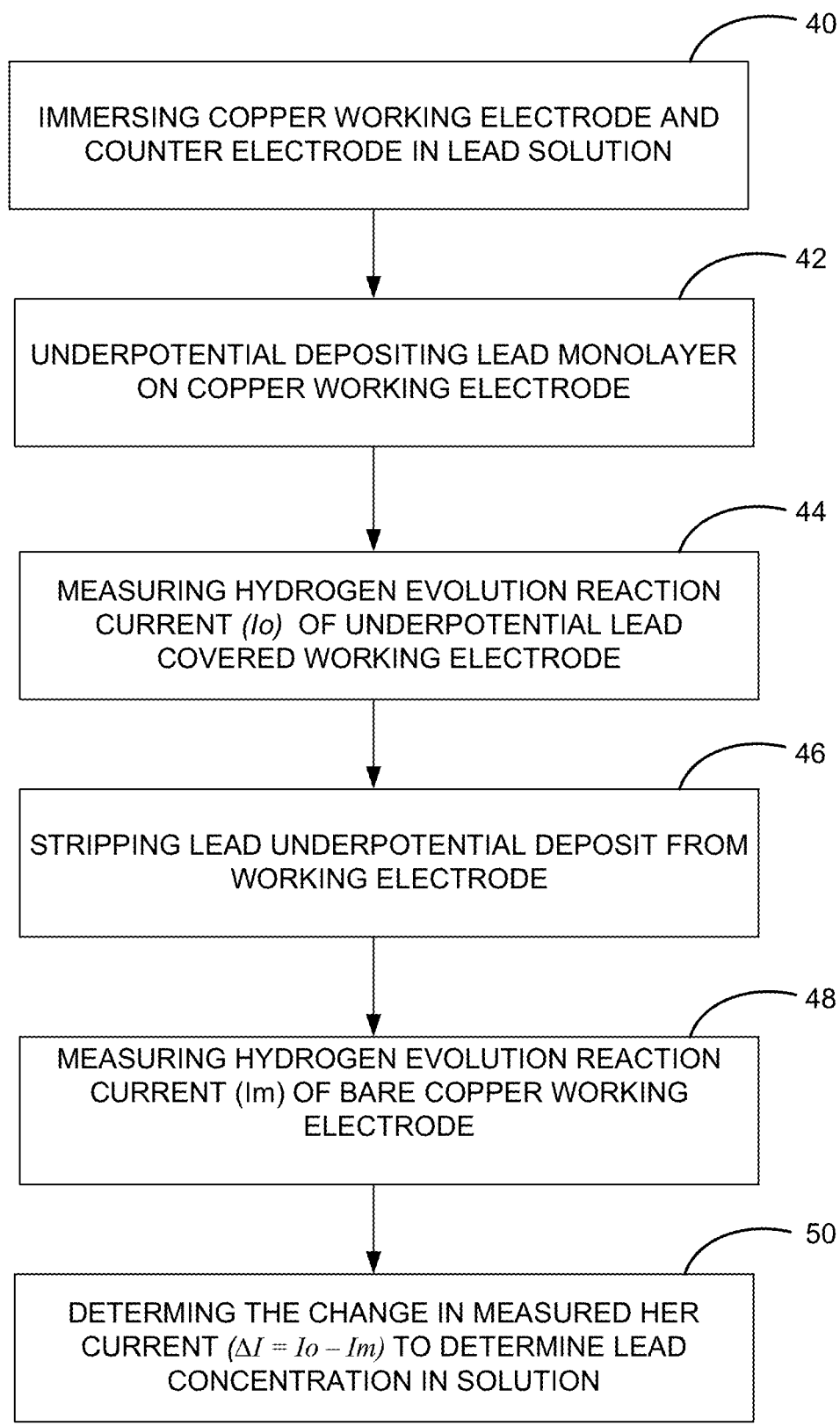
FIG. 2 is a flow chart illustrating a method of measuring lead concentrations in a sample using an electrochemical sensor as described herein.

FIG. 2 is a flow chart illustrating a method of measuring lead concentrations in a sample, such as drinking water, using an electrochemical sensor as described herein. In the method, at 40, a copper working electrode of the sensor is immersed in a lead-contaminated solution. At 42, the copper electrode is biased at a suitable (cathodic) potential that facilitates underpotential deposition of a lead monolayer on the copper surface. The coverage of the lead on the copper surface depends on time and the lead ion ($Pb^{+2}$) concentration in the sample. As lead covers the copper surface, it suppresses the ability of the surface to electrolyze water and evolve hydrogen gas. At 44, the hydrogen evolution reaction (HER) current of the underpotential lead covered electrode is then measured. Following measurement of the hydrogen evolution current of the underpotential lead covered electrode, at 46, the underpotentially deposited lead can be stripped to recover the bare copper surface. At 48, the hydrogen evolution baseline current (Ib) on the blank (Pb-free) copper electrode is then measured. At 50, the change in hydrogen evolution current $\Delta I = Ib - Im$ is calculated by a controller to determine the concentration of lead in the sample and provide an output of lead concentration in the sample to a display device (not shown). For a given underpotential deposition time, higher lead concentration in the sample provides a larger lead underpotential deposition coverage on the copper working electrode, and thus a larger suppression of the hydrogen evolution current.

By way of example, a Cu wafer with surface area of 1 cm$^2$ was used as the working electrode, Ag/AgCl electrode served as the reference electrode and a Pt wire served as the counter electrode. Electrolytes were prepared utilizing deionized water with 10 mM perchloric acid and with varying concentrations of $Pb^{2+}$ (10 ppb 1 ppm). A potentiostat with data acquisition was used for the electrochemical measurements.

The pre-cleaned copper working electrode was immersed into the $Pb^{+2}$-containing electrolyte. Underpotential deposition ($_{UPD}$) of lead was performed on the copper surface at an applied potential of −0.4 V vs. Ag/AgCl for a set time period t. After lead $_{UPD}$ surface coverage on Cu increased (surface coverage depends on $_{UPD}$ time t and concentration [$Pb^{2+}$]), the electrode potential was immediately switched to −0.8 V vs. Ag/AgCl for 50 s to measure the hydrogen evolution current (Im). Stripping coulometry was employed to strip the underpotentially deposited lead at an applied potential of −0.2 V vs. Ag/AgCl for 50 s to recover the bare copper surface. The hydrogen evolution baseline current (Ib) on the blank (Pb-free) Cu substrate was then measured at an applied potential of −0.8 V vs. Ag/AgCl for 50 s; (v) The change in hydrogen evolution current $\Delta I = Ib - Im$ was calculated. $\Delta I$ is related to the hydrogen evolution suppression due to underpotentially deposited lead and thus is a measure of the lead concentration in the test solution. For a given $_{UPD}$ time, higher $Pb^{+2}$ concentration in the sample solution will provide a larger Pb $_{UPD}$ coverage on Cu, and thus a larger suppression of the hydrogen evolution current.

Figure 3:
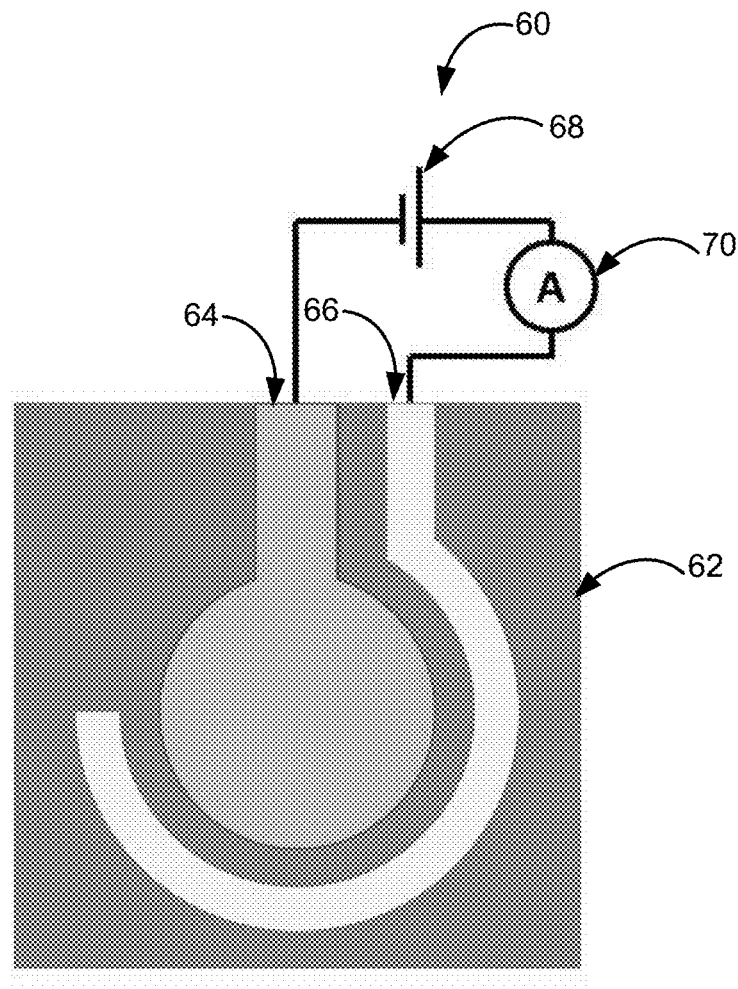
FIG. 3 is a schematic of the electrochemical sensor chip in accordance with an embodiment described herein. The center circular electrode is a copper working electrode and the surrounding concentric electrode is a platinum counter electrode. The two electrodes are connected to an external power supply and an ammeter.

In some embodiments, as shown in FIG. 3 the sensor 60 can include a substrate 62, a copper working electrode 64 formed on a surface of the substrate 62, and a counter electrode 66 formed on the surface of the substrate 62. The counter electrode 66 can include a metalized film, such as gold, platinum, palladium, silver, carbon, alloys thereof, and composites thereof. The films used to form the working electrode 64, counter electrode 66, and optional reference electrode (not shown) can be provided on the surface of the substrate 62 by using a thin film, thick film, and/or ink-jet printing technique, especially for the deposition of multiple electrodes on a substrate. The thin film process can include physical or chemical vapor deposition.

External power supply 68 and ammeter 70 can be incorporated together with a controller (not shown) and essential automation in a handheld sensor (not shown) that can work autonomously. The two electrodes can be incorporated into a one-time use chip that can be attached to the handheld device.

In some embodiments, the working electrode, counter electrode, and optional reference electrode may be formed using laser ablation, a process which can produce elements with features that are less than one-thousandth of an inch. Laser ablation enables the precise definition of the working electrode, counter electrode, and reference electrode as well as electrical connecting leads and other features, which is required to reduce coefficient of variation and provide accurate measurements. Metalized films, such as Cu, Au, Pd, and Pt or any metal having similar electrochemical properties, that can be sputtered or coated on plastic substrates, such as PET or polycarbonate, or other dielectric material, can be irradiated using laser ablation to provide these features.

Figure 4A:
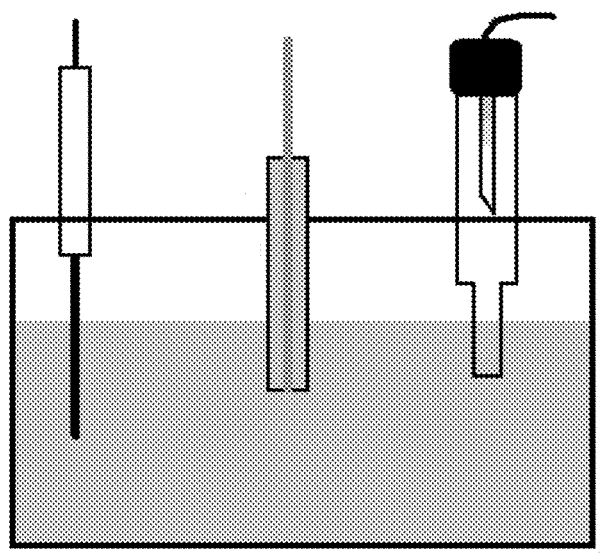
FIG. 4(A-C) are schematic illustrations of a method of forming a copper working electrode having a needle-like dendrite surface profile.
Figure 4B:
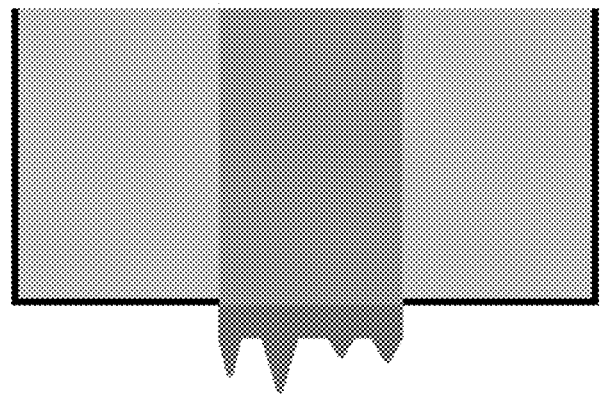
Figure 4C:
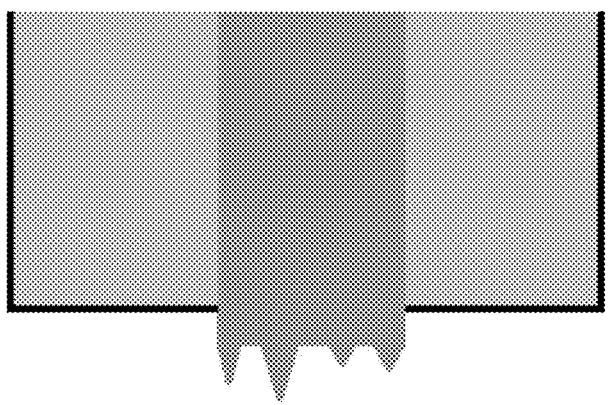

In some embodiments, in order to decrease the lead sensing time of the sensor, the copper working electrode can have an irregular needle-like dendrite surface profile as opposed to a planar surface. As illustrated in FIGS. 4(A-C), the irregular needle-like dendrite surface profile can be provide on a planar copper working electrode by placing a copper working electrode having a planar surface, a zinc counter electrode, and a Hg/HgO reference electrode in a 0.1 ZnO and KOH electrolyte (FIG. 4A). Zinc needle-like dendrites are then are then formed the copper working electrode surface by zinc dentrite potentiostatic electroplating (e.g., −1.6V v. Hg/HgO for 500 s) (FIG. 4B). The zinc dendrite plated copper working electrode, counter electrode, and reference electrode are provided in a Cu electroplating solution and copper layer is electroplated on the zinc dendrites to provide working electrode with a copper needle-like dendrite surface profile (FIG. 4C).

Figure 5:
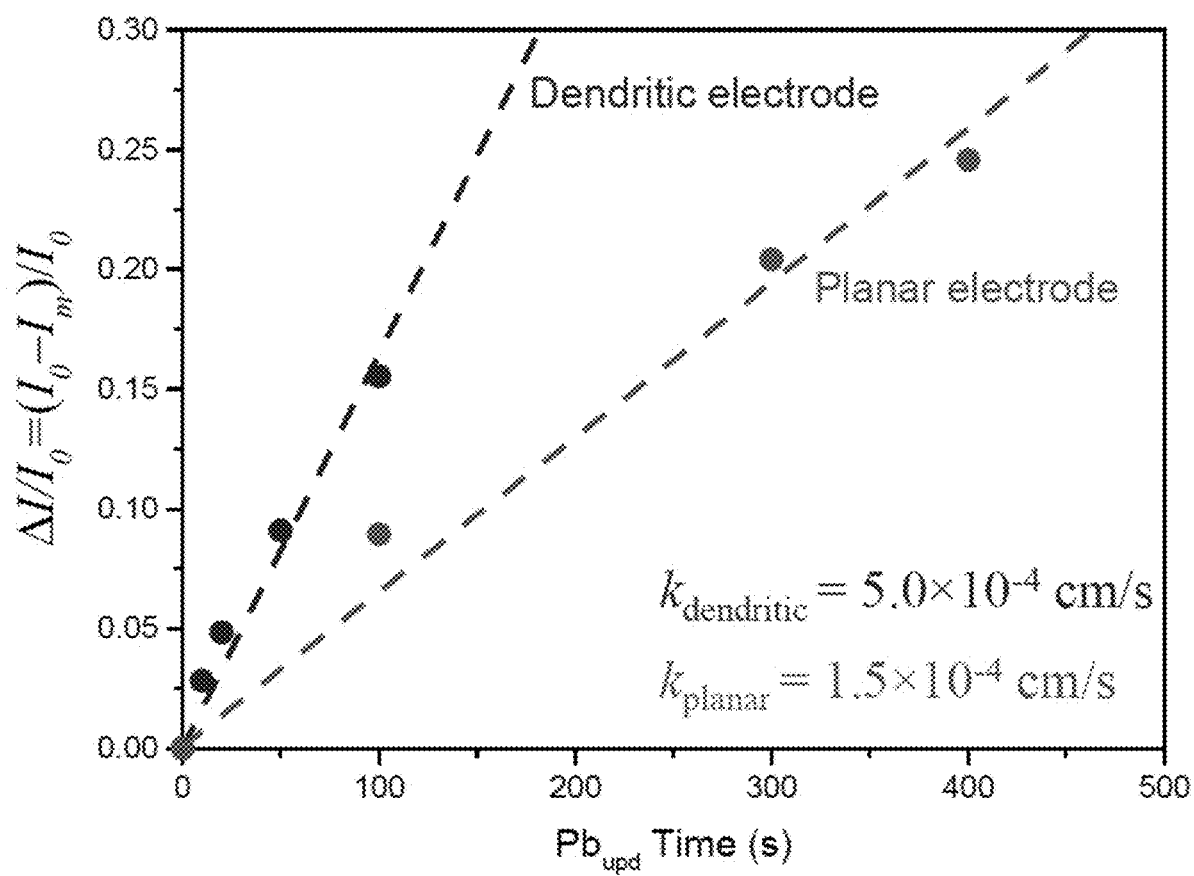
FIG. 5 illustrates a chart comparing hydrogen evolution current $\Delta I/I_0$ relative to the Pb under potential deposition time $t_{upd}$ for an aqueous 10 mM $HCLO_4$ and 1 ppm Pb2+ solution detected using a copper working electrode with needle-like dendrite surface profile and a copper working electrode with a planar surface profile.

FIG. 5 illustrates a chart comparing hydrogen evolution current $\Delta I/I_0$ relative to the Pb under potential deposition time $t_{upd}$ for an aqueous 10 mM $HCLO_4$ and 1 ppm Pb2+ solution detected using a copper working electrode with needle-like dendrite surface profile and a copper working electrode with a planar surface. The chart shows the copper working electrode having an irregular needle-like dendrite surface profile as opposed to a planar surface has a decrease in lead sensing time with a rate constant $k_{dendritic}$ of $5.0 \times 10^{-4}$ cm/s compared to $k_{planar}$ of $1.5 \times 10^{-4}$ cm/s.

The Example that follows illustrates embodiments of the present invention and are not limiting of the specification and claims in any way.

Example

In this Example, we developed an electrochemical lead (Pb) sensor based on the principle of lead underpotential deposition ($Pb_{upd}$). Pb exhibits $_{UPD}$ on copper (Cu). At suitable electrode potentials, a Cu electrode can be coated with a monolayer of $Pb_{upd}$. The $Pb_{upd}$ surface coverage on Cu depends on the $_{UPD}$ time ($t_{upd}$) and the $Pb^{2+}$ concentration. The $Pb_{upd}$ layer when formed on Cu, depending on its coverage (θ), suppresses the hydrogen evolution reaction (HER) current. The extent of HER suppression provides reliable quantification of the Pb surface coverage and thus the $Pb^{2+}$ concentration in solution. In this Example, we report the feasibility of this sensing concept for detecting $Pb^{2+}$ in the 10 ppb range in aerated electrolytes.

Deposition of $Pb_{upd}$ on Cu $Pb_{upd}$ deposition was performed in a three-electrode setup comprised of a sputter-deposited Cu substrate as the working electrode (area=1 cm2), a saturated Ag/AgCl (Fisher Scientific) reference electrode, and a Pt wire as counter electrode. The Cu substrate was pretreated in acid (2M $H_2SO_4$) for 60 s followed by a DI water rinse. An electrolyte containing 10 mM perchloric acid ($HClO_4$, Fisher Scientific) and various concentrations (10 ppb, 100 ppb and 1 ppm) of lead perchlorate [$Pb(ClO_4)_2$, 99% purity, Acros Organics] was employed. The electrolyte was prepared using 18 MΩ-cm DI water. Such an electrolyte, although idealized compared to actual water samples, was deemed appropriate for demonstrating the basic sensor operation. For $Pb_{upd}$ characterization, the electrolyte was de-aerated; however, for $Pb^{2+}$ detection, de-aeration was not applied. $Pb_{upd}$ was performed on Cu at an applied potential of −0.4 V vs. Ag/AgCl for various time periods ($t_{upd}$). To quantify the coverage of $Pb_{upd}$ on Cu, anodic stripping coulometry was used in which the $Pb_{upd}$ layer was potentiostatically stripped at 0.2 V vs. Ag/AgCl for 50 s and the net stripping charge density (Q) was measured.

Figure 6A:
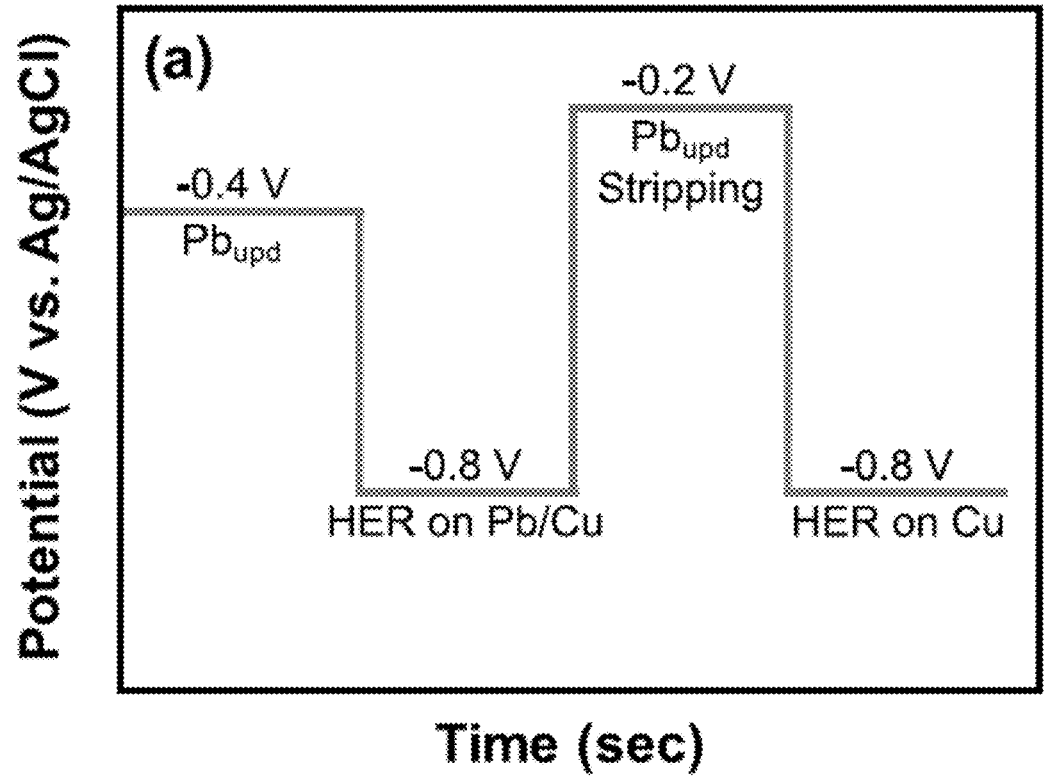
FIGS. 6(A-B) are a schematic describing operation of the electrochemical $Pb^{2+}$ sensor. The applied electrode potential (A) and the measured current response (B) are shown.

Measurement of the HER Current on
$Pb_{upd}$-Modified Cu for Quantifying $Pb^{2+}$
Concentration In aerated electrolytes, $Pb_{upd}$ deposition on Cu was followed by measurement of the HER current. Sensor operation consisted of the following stepwise sequence (FIG. 6) implemented in electrolytes containing $Pb^{2+}$ in the 10 ppb-1 ppm range:

(i) $Pb_{upd}$ deposition onto Cu at 0.4 V vs. Ag/AgCl for $t_{upd}$ ranging from 100-30000 s.

(ii) Measurement of the HER current ($I_m$) on $Pb_{upd}$-modified Cu by switching the applied potential to −0.8 V vs. Ag/AgCl and allowing the HER current to reach steady-state in 50 s. Note that, at −0.8 V, background currents due to Pb deposition and $O_2$-reduction (ORR) may be present but these do not affect sensing as discussed below.

Figure 6B:
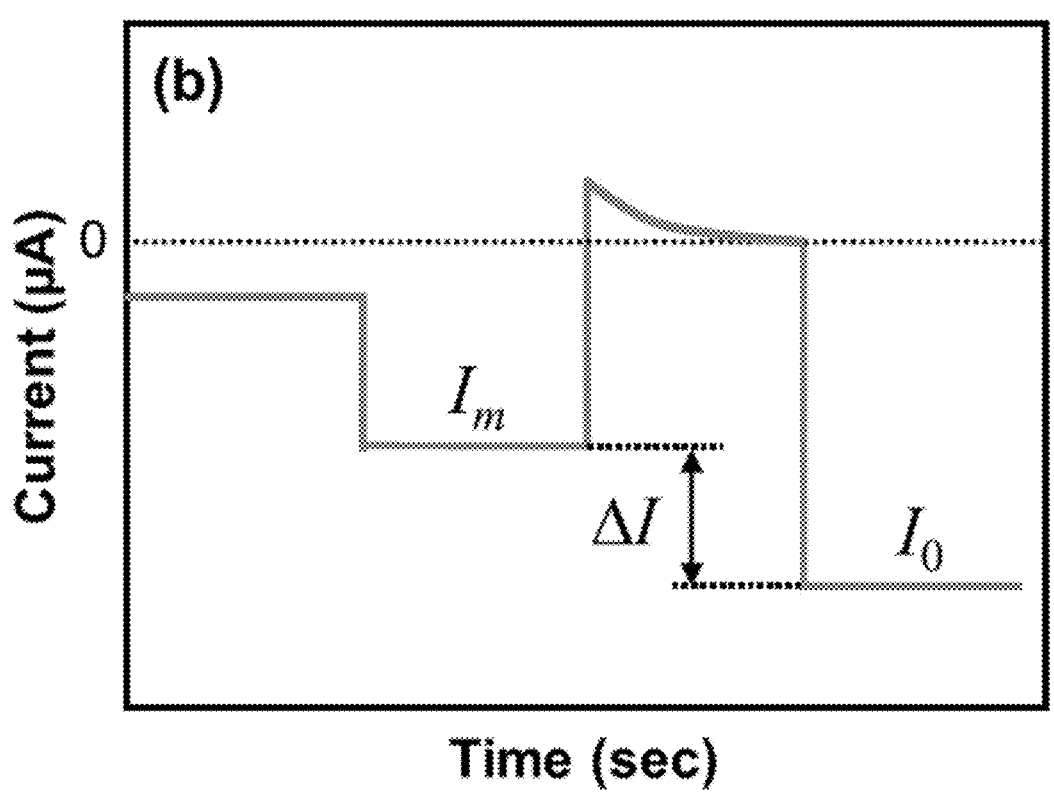

(iii) Stripping of the $Pb_{upd}$ layer formed in (i) at −0.2 V vs. Ag/AgCl to recover the bare Cu surface, followed by measurement of the HER current ($I_0$) on the bare Cu at −0.8 V. The current response to switching of the potential in steps (i)-(iii) is schematically shown in FIG. 6B. After implementing steps (i)-(iii), the change in HER current $\Delta I$ is computed:

$$\Delta I = I_0 - I_m \quad [1]$$

$\Delta I$ represents the suppression of HER due to the presence of underpotentially deposited Pb on the Cu electrode. As $Pb_{upd}$ time in step (i) increases, the Pb coverage θ also increases and this causes an increase in $\Delta I$. The concentration dependence of this $\Delta I$-$t_{upd}$ relationship is the foundational principle of operation of the sensor.

Results

Characteristics of $Pb_{upd}$ Formation on Cu

Figure 7:
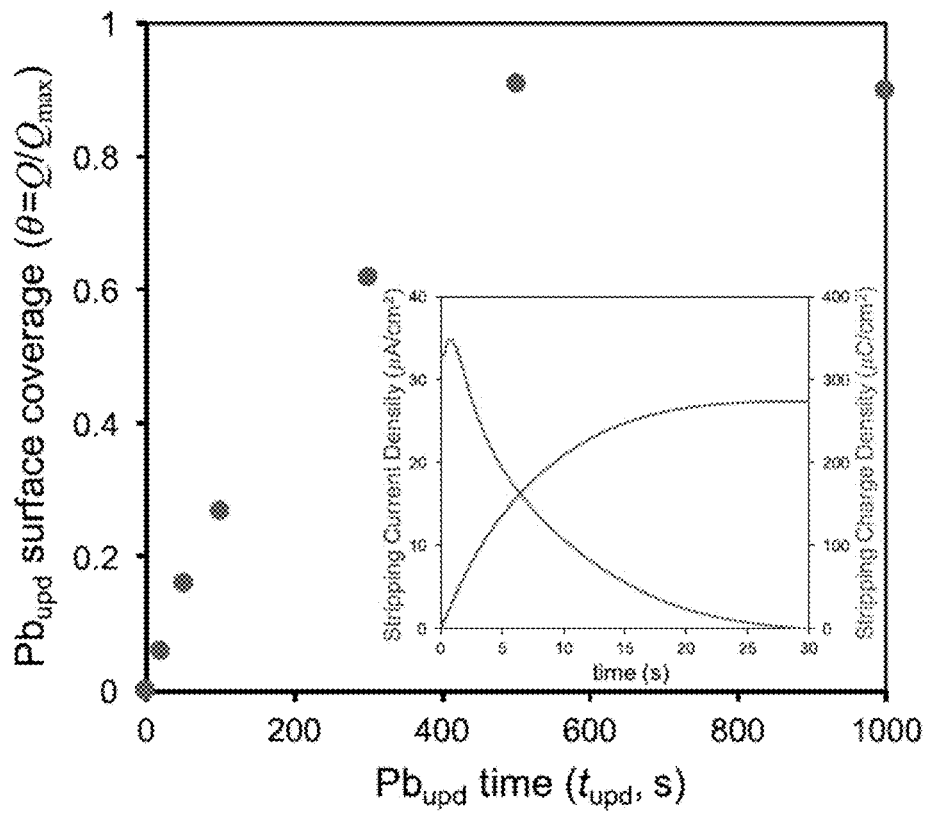
FIG. 7 illustrates $Pb_{upd}$ surface coverage (θ) increases linearly with $t_{upd}$ until surface saturation is reached at ~500 s. Inset shows the current (left axis) and charge (right axis) transients recorded during $Pb_{upd}$ stripping from which θ can be computed using Eq. [2].

FIG. 7 shows the dependence of $Pb_{upd}$ coverage on deposition time at −0.4 V vs. Ag/AgCl for an electrolyte containing 1 ppm of $Pb^{2+}$. The coverage θ was calculated by stripping the $Pb_{upd}$ layer, measuring the stripping charge density (Q, as shown in FIG. 3 inset), and then applying the equation:

$$\theta = \frac{Q}{Q_{max}} \quad [2]$$

where $Q_{max}$ represents the charge density associated with saturation surface concentration of $Pb_{upd}$ where all surface sites available for $_{UPD}$ are occupied (300 μC/cm²). FIG. 3 shows that θ increases linearly with time at short times (t<100 s) and θ reaches saturation at long times (t>500 s). The time-dependence of θ is related to diffusion and surface reaction rates, and thus is affected by the $Pb^{2+}$ concentration in solution.

HER Suppression on $Pb_{upd}$-Modified Cu

Figure 8:
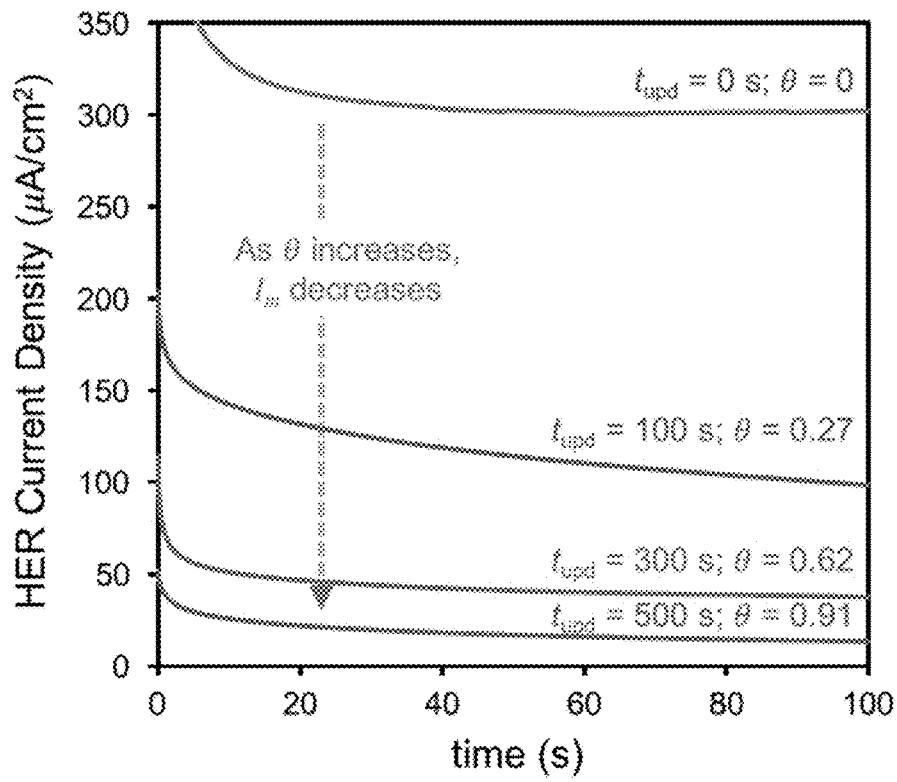
FIG. 8 illustrates the HER current ($I_m$) decreases as the $Pb_{upd}$ coverage increases. $Pb^{2+}$ concentration was 1 ppm.

As $Pb_{upd}$ covers the Cu surface, it suppresses $H_2$ evolution because of the very low exchange current density for HER on Pb. FIG. 8 shows HER current densities (at −0.8 V) on $Pb_{upd}$-modified Cu where the $Pb_{upd}$ was performed for $t_{upd}$=0, 100, 300 and 500 s from a 1 ppm $Pb^{2+}$-containing solution. It is noted that HER current density drops from 300 μA/cm² for $t_{upd}$=0 s (i.e., θ=0) to merely 30 μA/cm2 for $t_{upd}$=500 s (i.e., θ =0.91 from FIG. 7). The suppression of HER current is thus an indirect measure of the Pb coverage. For a fixed $t_{upd}$, the Pb coverage is in turn a function of the $Pb^{2+}$ concentration, as discussed below. A benefit of measuring HER current at a potential of −0.8 V is that its magnitude (~300 μA/cm2 on bare Cu) is at least ten times larger than currents due to competing reactions: (i) Electrodeposition of Pb may occur in parallel to HER; however, mass-transport limited Pb electrodeposition proceeds at a meagre ~1 μA/cm₂current even at 1 ppm $Pb^{2+}$ in solution; and (ii) Even in the presence of dissolved $O_2$, the ORR current is 20-40 μA/cm2. Thus, suppression of the high (~300 μA/cm2) HER current due to $Pb_{upd}$ formation is detectable even in the presence of such background currents.

Figure 9A:
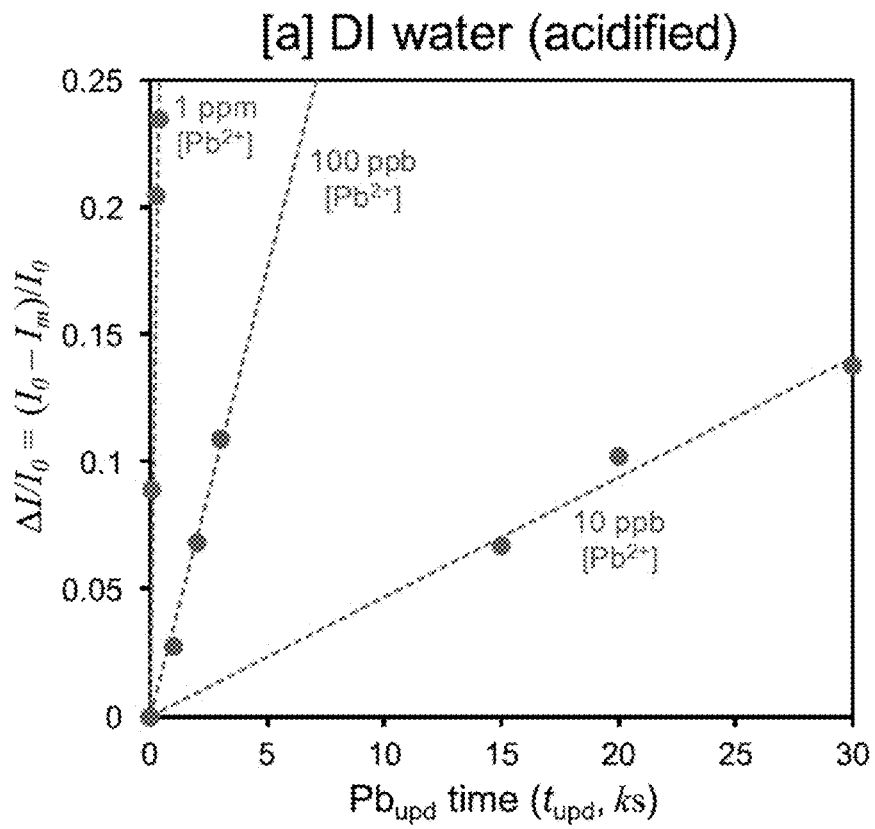
FIG. 9 is a calibration chart showing the dependence of $\Delta I/I_0$ on $t_{upd}$ and $[Pb^{2+}]$. For a fixed $t_{upd}$, $\Delta I/I_0$ can be measured and this enables determination of $[Pb^{2+}]$.
Figure 9B:
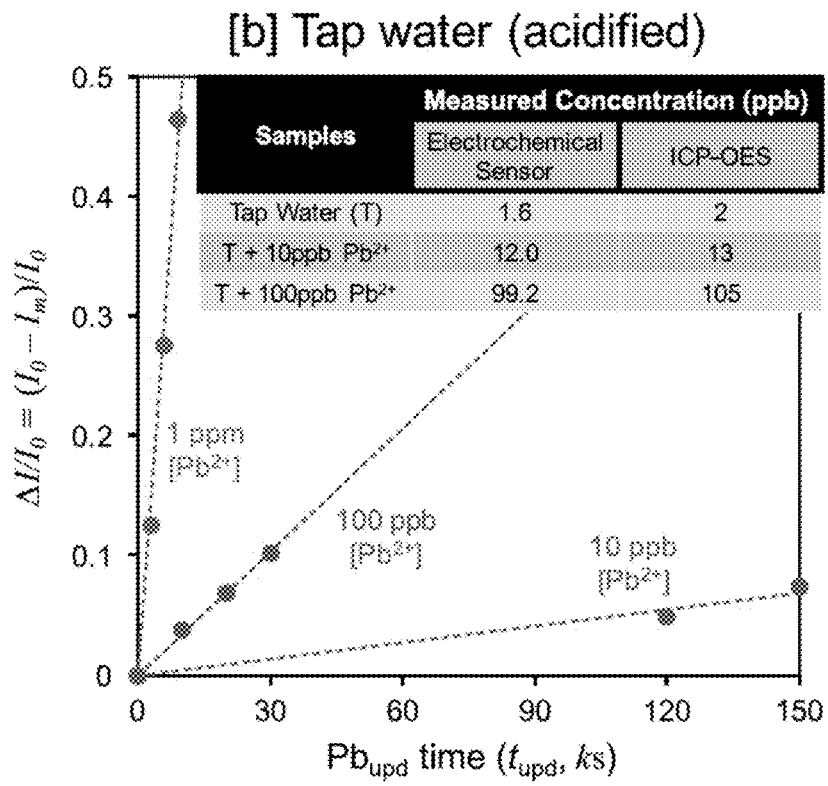

FIG. 9 shows the measured change in hydrogen evolution current (ΔI) for aerated electrolytes with various concentrations of $Pb^{2+}$ (1 ppm, 100 ppb and 10 ppb). The ratio ΔI/I0 is seen to be a linear function of $t_{upd}$ and is seen to depend on the $Pb^{2+}$ concentration. This provides a calibration chart for the electrochemical sensor. In an actual sensor, for a known value of $t_{upd}$ and a measured value of ΔI/I0, a unique $Pb^{2+}$ concentration exists which can then be estimated from data in FIG. 9. Note that the linear dependence of ΔI/I0 on $t_{upd}$ is measurable down to $Pb^{2+}$ concentration of ΔI/I0 ppb which is the desired range for practical applications. Further, FIG. 9 was obtained in the absence of any de-aeration, which confirms that the sensing method functions even in the presence of background ORR currents.

Quantifying the dependence of ΔI/I0 on $Pb^{2+}$ concentration and $Pb_{upd}$ time ($t_{upd}$)

As shown in FIG. 9, $\Delta I/I_0$ depends on the $Pb^{2+}$ concentration and on $t_{upd}$. We now examine this dependence quantitatively. Assuming the $Pb_{upd}$ formation process to be analogous to first-order surface adsorption, the time-dependent Pb surface coverage obeys:

$$\Gamma \frac{d\theta}{dt} = kC(1-\theta) \quad [3]$$

where Λ is the Pb saturation surface concentration (1.55× $10^{-9}$ mol/cm²), Cb is the $Pb^{2+}$ concentration, and k is a rate constant. Initially (t=0), the coverage θ=0. Furthermore, when θ is small, Eq. [3] yields:

$$\theta \cong \frac{kC_b}{\Gamma} t_{upd} \quad [4]$$

On $Pb_{upd}$-covered sites on the Cu electrode, the HER current is negligibly small. Thus, HER proceeds only on exposed Cu sites at a current given as:

$$I_m = I_0(1-\theta) \quad [5]$$

Combining Eqns. [1], [4] and [5], ΔI/I0 exhibits the following dependence on $C_b$ and $t_{upd}$:

$$\frac{\Delta I}{I_0} = \left(\frac{kCb}{\Gamma}\right) t_{upd} \quad [6]$$

First, the linear dependence of ΔI/I0 on $t_{upd}$ seen in Eq. [6] is consistent with experimental data (FIG. 9). Second, the slope of ΔI/I0 vs. $t_{upd}$ is kCb/Λ, i.e., the slope increases linearly with the $Pb^{2+}$ concentration also consistent with FIG. 9. The measured slopes (from FIG. 9) for various $Pb^{2+}$ concentrations are listed in the Table. From these slopes, the rate constant k was estimated (Table) and found to be of the order $~10^{-4}$ cm/s independent of $C_b$. This is significant because, for diffusion-limited adsorption, k approaches D/δ, where D is the $Pb^{2+}$ diffusion coefficient (=-$10^{-5}$ cm₂/s) and δ is the boundary layer thickness (taken as 0.05 cm). For these estimated values of D and δ, we get k=2×10-4 cm/s and thus within the same range as that measured experimentally (Table). This order of magnitude calculation establishes that the $Pb_{upd}$ step is limited by slow $Pb^{2+}$ diffusion, and thus this step may dictate the sensor response time especially when analyzing low ppb-levels of Pb.

TABLE

Analysis of ΔI/I0 vs. $t_{upd}$ data presented in FIG. 9

| [$Pb^{2+}$] (ppb) | Slope of ΔI/I0 vs. $t_{upd}$ (FIG. 5) | k (cm/s) |
| --- | --- | --- |
| 10 | 4.68 × $10^{-6}$ | 1.45 × $10^{-4}$ |
| 100 | 3.67 × $10^{-5}$ | 1.14 × $10^{-4}$ |
| 1000 | 5.84 × $10^{-4}$ | 1.81 × $10^{-4}$ |

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A sensor for detecting lead in an aqueous solution, the sensor comprising:
   a copper working electrode for placement in the aqueous solution,
   a counter electrode for placement in the aqueous solution,
   a power supply for applying underpotential deposition of lead ($Pb_{upd}$) onto the copper electrode,
   a measuring device for providing measurement of a hydrogen evolution reaction (HER) current on a $Pb_{upd}$-modified electrode, and
   a controller configured to correlate the degree of suppression of the HER current to $Pb_{upd}$ coverage to determine the lead coverage and lead concentration of the solution.

2. The sensor of claim 1, wherein the counter electrode comprises gold, platinum, palladium, silver, carbon, or alloys thereof.

3. The sensor of claim 1, further comprising a reference electrode.

4. The sensor of claim 1, wherein the copper working electrode has a needle-like dendritic surface profile.

5. The sensor of claim 4, wherein the needle-like dendritic surface profile of the copper working electrode is defined by an under Zn dendrite potentiostatic plating.

* * * * *